United States Patent
Nakagawa (10) Patent No.: US 10,568,491 B2
(45) Date of Patent: Feb. 25, 2020

(54) ENDOSCOPE

(71) Applicant: OLYMPUS CORPORATION, Tokyo (JP)

(72) Inventor: Yusuke Nakagawa, Nagano (JP)

(73) Assignee: OLYMPUS CORPORATION, Tokyo (JP)

(*) Notice: Subject to any disclaimer, the term of this patent is extended or adjusted under 35 U.S.C. 154(b) by 389 days.

(21) Appl. No.: 15/163,784

(22) Filed: May 25, 2016

(65) Prior Publication Data
US 2016/0262599 A1     Sep. 15, 2016

Related U.S. Application Data (63) Continuation of application No. PCT/JP2014/074546, filed on Sep. 17, 2014.

(30) Foreign Application Priority Data

Nov. 28, 2013  (JP) .................................. 2013-246147

(51) Int. Cl.
*A61B 1/00* (2006.01)
*A61B 1/05* (2006.01)
*A61B 1/005* (2006.01)

(52) U.S. Cl.
CPC .......... *A61B 1/00165* (2013.01); *A61B 1/005* (2013.01); *A61B 1/00013* (2013.01);
(Continued)

(58) Field of Classification Search
CPC ............ A61B 1/00165; A61B 1/00013; A61B 1/00075; A61B 1/00096; A61B 1/005; A61B 1/0057
(Continued)

(56) References Cited

U.S. PATENT DOCUMENTS 5,247,596 A * 9/1993 Maignan .............. G02B 6/4202
                                                              257/E25.032
6,411,761 B1 * 6/2002 Yokokawa ........... G02B 6/4433
                                                              385/102
(Continued)

FOREIGN PATENT DOCUMENTS

JP    2000-126111 A    5/2000
JP    2008-253774 A    10/2008
(Continued)

OTHER PUBLICATIONS

International Search Report dated Oct. 28, 2014 issued in PCT/JP2014/074546.
(Continued)

*Primary Examiner* — Timothy J Neal
*Assistant Examiner* — Jae Woo
(74) *Attorney, Agent, or Firm* — Scully, Scott, Murphy & Presser, P.C.

(57) ABSTRACT

An endoscope includes an insertion portion in which a rigid distal end portion, a bending portion, and a flexible portion are provided in a connected row arrangement, and an optical fiber that is inserted through the insertion portion. The endoscope has, in the rigid distal end portion, an optical transmission module in which an image pickup device, an optical device in which a light-emitting portion is formed, and a holding member that has a through hole. A length in the bending portion of the optical fiber whose distal end portion is inserted into and fixed in the through hole of the holding member is longer than a length L0 of the bending portion.

6 Claims, 9 Drawing Sheets

(52) U.S. Cl.
CPC ........ *A61B 1/0057* (2013.01); *A61B 1/00075* (2013.01); *A61B 1/00096* (2013.01); *A61B 1/05* (2013.01)

(58) Field of Classification Search
USPC ........................................................ 600/129
See application file for complete search history.

(56) References Cited

U.S. PATENT DOCUMENTS

| | | | | |
|---|---|---|---|---|
| 6,529,662 | B1* | 3/2003 | Kobayashi | G02B 6/4432 |
| | | | | 385/112 |
| 7,129,472 | B1* | 10/2006 | Okawa | A61B 1/00059 |
| | | | | 250/234 |
| 7,435,215 | B2* | 10/2008 | Seto | A61B 1/0051 |
| | | | | 600/106 |
| 9,439,554 | B2* | 9/2016 | Usami | A61B 1/00004 |
| 9,445,709 | B2* | 9/2016 | Nakamura | A61B 1/00036 |
| 9,625,664 | B2* | 4/2017 | Motohara | G02B 6/4253 |
| 2008/0039686 | A1* | 2/2008 | Mori | A61B 1/00165 |
| | | | | 600/109 |
| 2013/0096380 | A1* | 4/2013 | Matsuzawa | A61B 1/00013 |
| | | | | 600/109 |
| 2013/0235175 | A1* | 9/2013 | Kazama | H04N 7/18 |
| | | | | 348/65 |
| 2014/0097459 | A1* | 4/2014 | Motohara | H01S 5/02252 |
| | | | | 257/98 |
| 2014/0221749 | A1* | 8/2014 | Grant | A61B 1/00183 |
| | | | | 600/112 |
| 2014/0320619 | A1* | 10/2014 | Nakamura | A61B 1/00036 |
| | | | | 348/65 |

FOREIGN PATENT DOCUMENTS

| | | |
|---|---|---|
| JP | 2013-025092 A | 2/2013 |
| WO | 93/23111 A1 | 11/1993 |
| WO | WO 2013/011983 A1 | 1/2013 |

OTHER PUBLICATIONS

Extended Supplementary European Search Report dated Jun. 26, 2017 in European Patent Application No. 14 86 5935.2.

* cited by examiner

ENDOSCOPE

CROSS REFERENCE TO RELATED APPLICATION

This application is a continuation application of PCT/JP2014/074546 filed on Sep. 17, 2014 and claims benefit of Japanese Application No. 2013-246147 filed in Japan on Nov. 28, 2013, the entire contents of which are incorporated herein by this reference.

BACKGROUND OF THE INVENTION

1. Field of the Invention

The present invention relates to a flexible endoscope in which an optical fiber of an optical transmission module that is arranged in a rigid distal end portion is inserted through an insertion portion.

2. Description of the Related Art

Endoscopes include an image pickup device such as a CCD in a distal end portion of an elongated flexible insertion portion. In recent years, the use of image pickup devices with a high pixel count in endoscopes is being studied. When an image pickup device with a high pixel count is used, because a signal amount that is transmitted to a signal processing apparatus (processor) from the image pickup device increases, optical signal transmission through a narrow optical fiber by means of optical signals is preferably employed instead of electrical signal transmission through metal wiring by means of electrical signals. In the optical signal transmission, an E/O module (electrical-optical converter) that converts electrical signals to optical signals, and an O/E module (optical-electrical converter) that converts optical signals to electrical signals are used.

For example, Japanese Patent Application Laid-Open Publication No. 2013-025092 discloses an optical transmission module including: an optical device that performs inputting or outputting of an optical signal; a substrate on which the optical device is mounted; and holding portions which have a through hole for inserting an optical fiber that is configured to transmit optical signals that are inputted to and outputted from the optical device, and which are arranged side by side in the thickness direction of the optical device.

SUMMARY OF THE INVENTION

An endoscope according to an embodiment of the present invention includes: an insertion portion in which a rigid distal end portion, a bending portion for changing a direction of the rigid distal end portion, and a flexible portion are provided in a connected row arrangement; and an optical fiber that is inserted through the insertion portion and is configured to transmit an optical signal, the endoscope having, in the rigid distal end portion, an optical transmission module in which an image pickup device, an optical device in which a light-emitting portion configured to convert an electrical signal that the image pickup device outputs into the optical signal is formed, and a holding member having a through hole and disposed so that the through hole is positioned over the light-emitting portion are arranged, wherein a length in the bending portion of the optical fiber whose distal end portion is inserted into and fixed in the through hole of the holding member is longer than a length of the bending portion.

DETAILED DESCRIPTION OF THE PREFERRED EMBODIMENTS

<First Embodiment>

Figure 1:
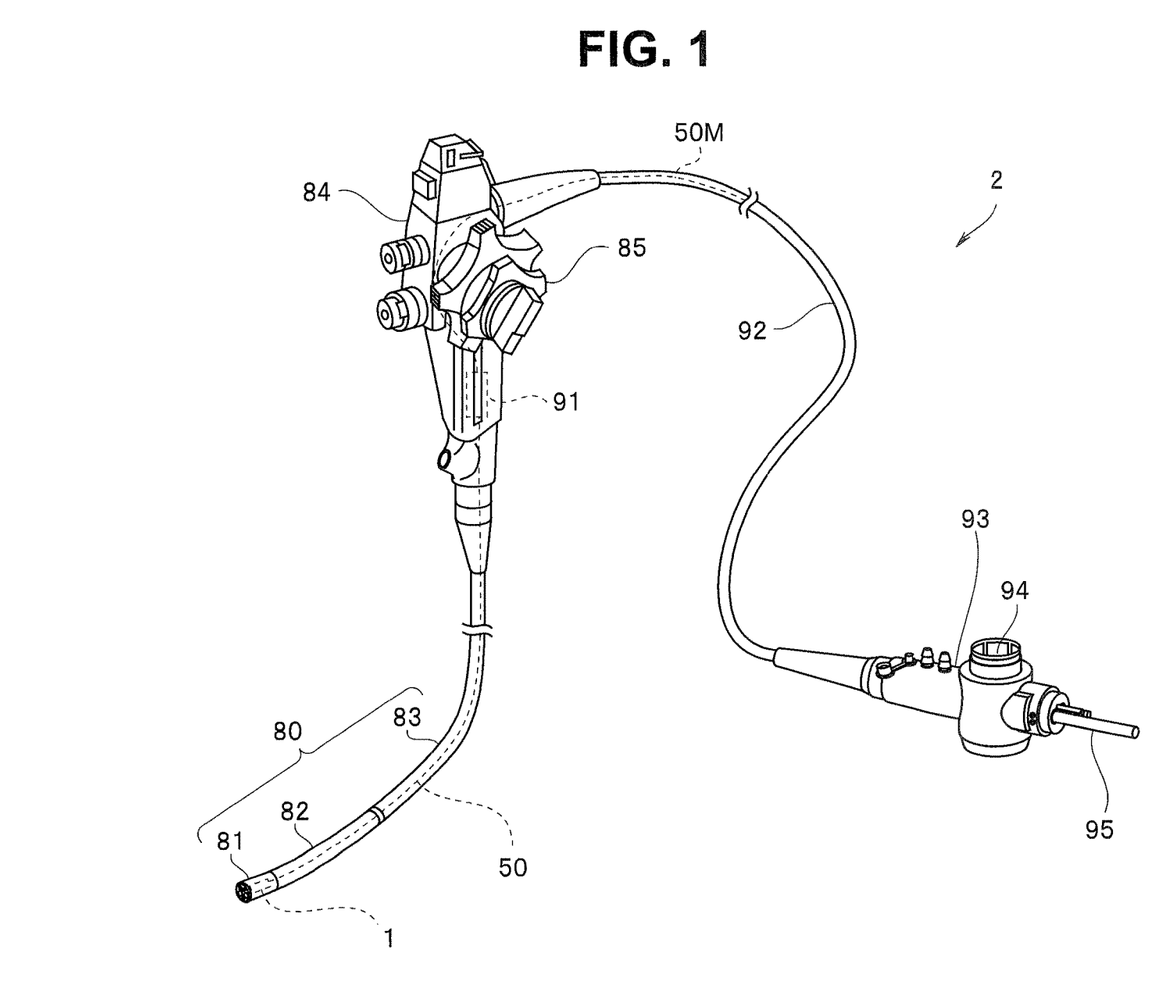
FIG. 1 is a perspective view of an endoscope of a first embodiment.

As shown in FIG. 1, an endoscope 2 of the present embodiment is a flexible endoscope that includes an insertion portion 80, an operation portion 84 that is arranged on a proximal end portion side of the insertion portion 80, a universal cord 92 that is extended from the operation portion 84, and a connector 93 that is arranged on a proximal end portion side of the universal cord 92.

The insertion portion 80 includes a rigid distal end portion 81, a bending portion 82 for changing a direction of the rigid distal end portion 81, and an elongated flexible portion 83 that are provided in a connected row arrangement.

An image pickup optical unit 90L, an image pickup device 90, and an optical transmission module 1 that is an E/O module that converts an image pickup signal (electrical signal) from the image pickup device 90 into an optical signal are arranged in the rigid distal end portion 81. The image pickup device 90 is a CMOS (complementary metal oxide semiconductor) image sensor or a CCD (charge coupled device) or the like.

Figure 2:
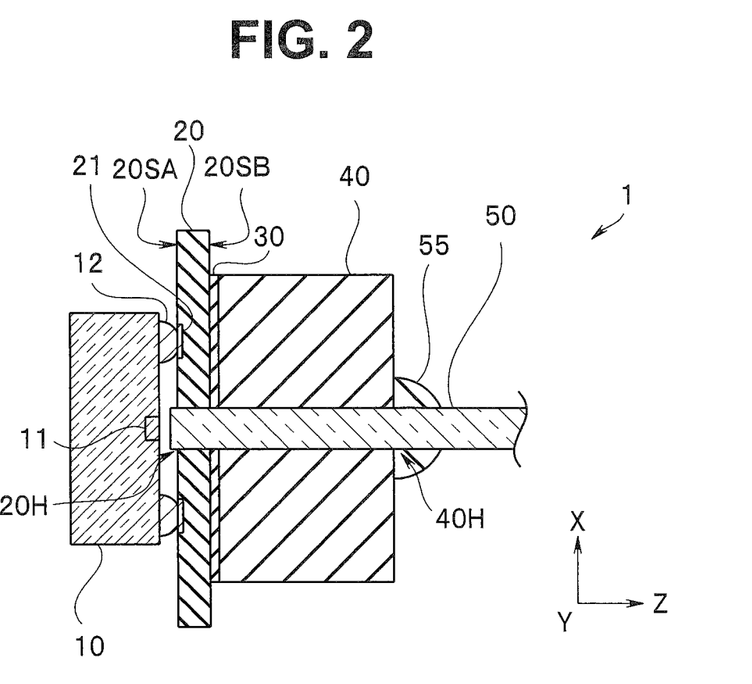
FIG. 2 is a cross-sectional view of an optical transmission module of the endoscope of the first embodiment.

As shown in FIG. 2, the optical transmission module 1 includes an optical device 10, a wiring board 20, a holding member (also referred to as a "ferrule") 40 and an optical fiber 50. In the optical transmission module 1, the optical device 10, the wiring board 20 and the holding member 40 are disposed side-by-side in a thickness direction (Z direction) of the optical device 10. The optical fiber 50 may be provided in a form in which the optical fiber 50 is housed inside an unshown protective tube. In such case, the optical fiber 50 is of a form that is freely movable to a certain extent inside the protective tube.

The optical device 10 is a surface-emitting laser chip having a light-emitting portion 11 that outputs light of an optical signal. For example, the ultra-small optical device 10 having dimensions in plan view of 250 μm×300 μm includes the light-emitting portion 11 having a diameter of 20 μm, and an electrode 12 that supplies a drive signal to the light-emitting portion 11 on a principal surface.

On the other hand, for example, the optical fiber 50 having a diameter of 125 μm includes a core having a diameter of 50 μm that transmits light, and cladding that covers an outer circumference of the core.

A distal end portion of the optical fiber 50 is inserted into a through hole 40H of the holding member 40 having a substantially rectangular parallelepiped shape that is bonded onto the optical device 10, and the distal end portion of the optical fiber 50 is fixed with an adhesive 55. Positioning between the light-emitting portion 11 of the optical device 10 and the optical fiber 50 is performed by inserting the optical fiber 50 into the through hole 40H.

A hole 20H that becomes an optical path is formed in the tabular wiring board 20 that has a first principal surface 20SA and a second principal surface 20SB. The optical device 10 is flip-chip mounted on the first principal surface 20SA in a state in which the light-emitting portion 11 thereof is disposed at a position facing the hole 20H of the wiring board 20. That is, the wiring board 20 has an electrode pad 21 to which a plurality of electrodes 12 of the optical device 10 are respectively joined. An FPC substrate, a ceramic substrate, a glass epoxy substrate, a glass substrate, a silicon substrate or the like is used as a substrate of the wiring board 20.

For example, Au bumps that are the electrodes 12 of the optical device 10 are ultrasonically joined with the electrode pad 21 of the wiring board 20. Note that, an adhesive such as an underfill material or a sidefill material may be injected into a joined portion.

The mounting may also be performed by printing a solder paste or the like on the wiring board 20, disposing the optical device 10 at a predetermined position thereon, and thereafter melting the solder by reflow soldering or the like. Note that, the wiring board 20 has an electrode pad (not illustrated) that is connected with the image pickup device 90 (FIG. 3) and metal wiring 90M (FIG. 3), and wiring (not illustrated) that transmits to the electrode pad 21 an electrical signal that is transmitted thereto from the image pickup device 90. The wiring board 20 may also include a processing circuit for converting an electrical signal that is transmitted thereto from the image pickup device 90 into a drive signal of the optical device 10.

As described already, the through hole 40H having a columnar shape, the inner diameter of which is substantially the same as the outer diameter of the optical fiber 50 to be inserted into the through hole 40H, is formed in the holding member 40. Here, the term "substantially the same" refers to both diameters being substantially the "same" size, such that an outer circumferential face of the optical fiber 50 and a wall face of the through hole 40H enter an abutting state. For example, the inner diameter of the through hole 40H is manufactured so as to be 1 μm to 5 μm larger than the outer diameter of the optical fiber 50.

Besides a columnar shape, the through hole 40H may have a prismatic shape as long as the optical fiber 50 can be held by a wall face thereof. The material of the holding member 40 is ceramic, Si, glass or a metal member such as SUS or the like. Note that the holding member 40 may also have a substantially columnar shape or a substantially conical shape or the like.

The holding member 40 is joined through an adhesive layer 30 to the second principal surface 20SB of the wiring board 20 in a state in which the through hole 40H is disposed at a position facing the hole 20H of the wiring board 20. Note that, for example, the adhesive layer 30 that is made of a thermosetting resin is not provided in a region at which the through hole 40H and the hole 20H face each other.

An angle knob 85 that is used to operate the bending portion 82, and an O/E module 91 that is an optical transmission module that converts an optical signal to an electrical signal are arranged on the operation portion 84. The connector 93 has an electrical connector portion 94 that is connected with a processor (not illustrated), and a light guide connection portion 95 that is connected with a light source. The light guide connection portion 95 is connected to an optical fiber bundle that guides an illuminating light to the rigid distal end portion 81. Note that the connector 93 may also have a configuration in which the electrical connector portion 94 and the light guide connection portion 95 are integrated.

In the endoscope 2, an image pickup signal is converted to an optical signal by the optical transmission module 1 of the rigid distal end portion 81, and the optical signal is then transmitted to the operation portion 84 through the narrow optical fiber 50 that is inserted through the insertion portion 80. The optical signal is then converted back to an electrical signal by the O/E module 91 arranged in the operation portion 84, and the electrical signal is transmitted to the electrical connector portion 94 through metal wiring 50M that is inserted through the universal cord 92. That is, a signal is transmitted through the optical fiber 50 inside the small-diameter insertion portion 80, while inside the universal cord 92 that is not inserted into the body and for which there is little restriction with respect to the outer diameter thereof, the signal is transmitted through the metal wiring 50M that is thicker than the optical fiber 50.

Note that, in a case where the O/E module 91 is arranged in the connector portion 94, the optical fiber 50 may be inserted through the universal cord 92 as far as the electrical connector portion 94. Further, if the O/E module 91 is arranged in the processor, the optical fiber 50 may be inserted through as far the connector 93.

The strength of an optical fiber in the longitudinal direction is not strong. Consequently, if tensile stress/compressive stress is repeatedly applied in the longitudinal direction to an optical fiber as a result of a flexible insertion portion of an endoscope changing shape, there is a possibility that the optical fiber will be damaged or broken. There is also a possibility that another member in the insertion portion 80 will become entangled with the optical fiber, and the optical fiber will be damaged. If the optical fiber is damaged or the like, transmission of optical signals is difficult.

If the insertion portion 80 changes shape, stress is applied to the optical fiber 50 that is inserted through the insertion portion 80 of the endoscope 2. In particular, the optical fiber 50 receives a large amount of stress when the insertion portion 80 changes shape due to a bending operation of the bending portion 82.

Figure 3:
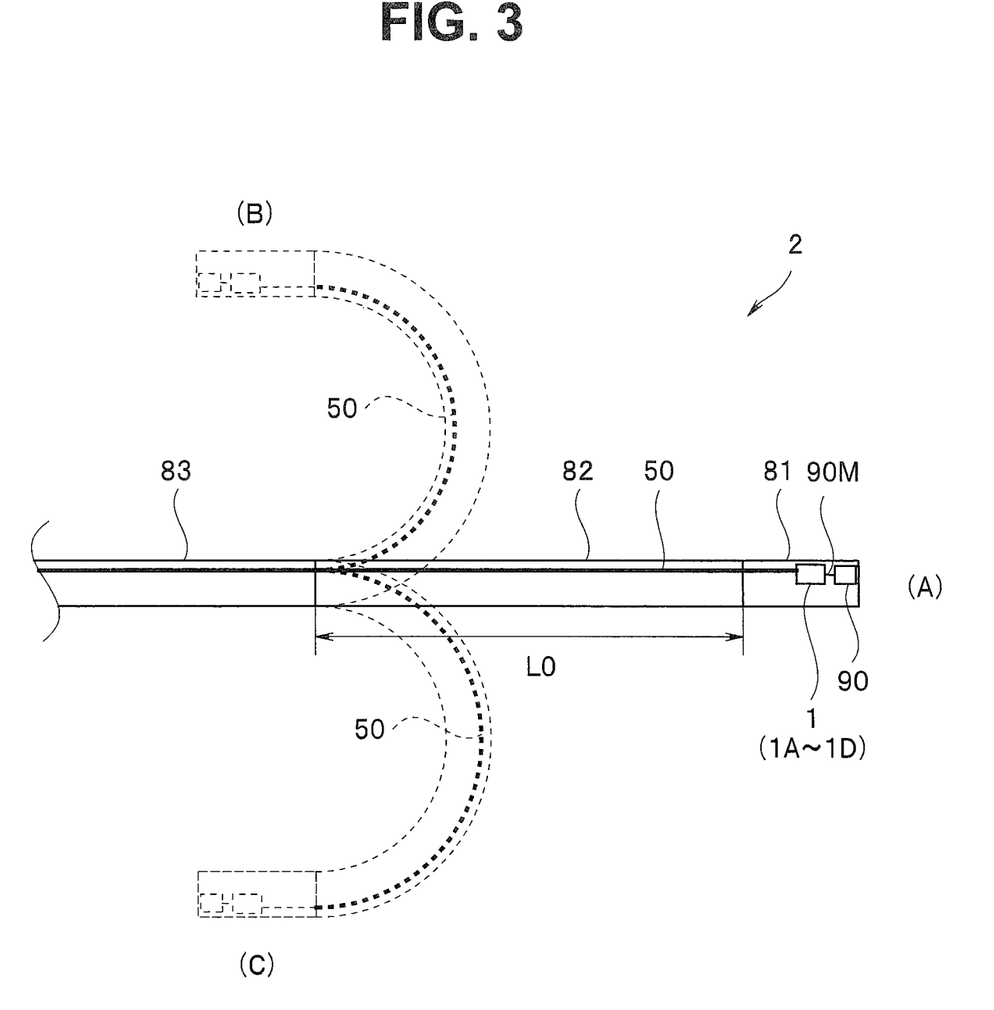
FIG. 3 is a cross-sectional view illustrating operations of a bending portion of the endoscope of the first embodiment.

As shown in FIG. 3, a path length L of the optical fiber 50 that is inserted through when the bending portion 82 is in a straight state (A) is taken as "L0". In this respect, when the bending portion 82 bends in a (B) direction, the path length L shortens, and hence there is a risk that compressive stress will be applied to the optical fiber 50. On the other hand, when the bending portion 82 bends in a (C) direction, the path length L lengthens, and hence there is a risk that tensile stress will be applied to the optical fiber 50.

Figure 4:
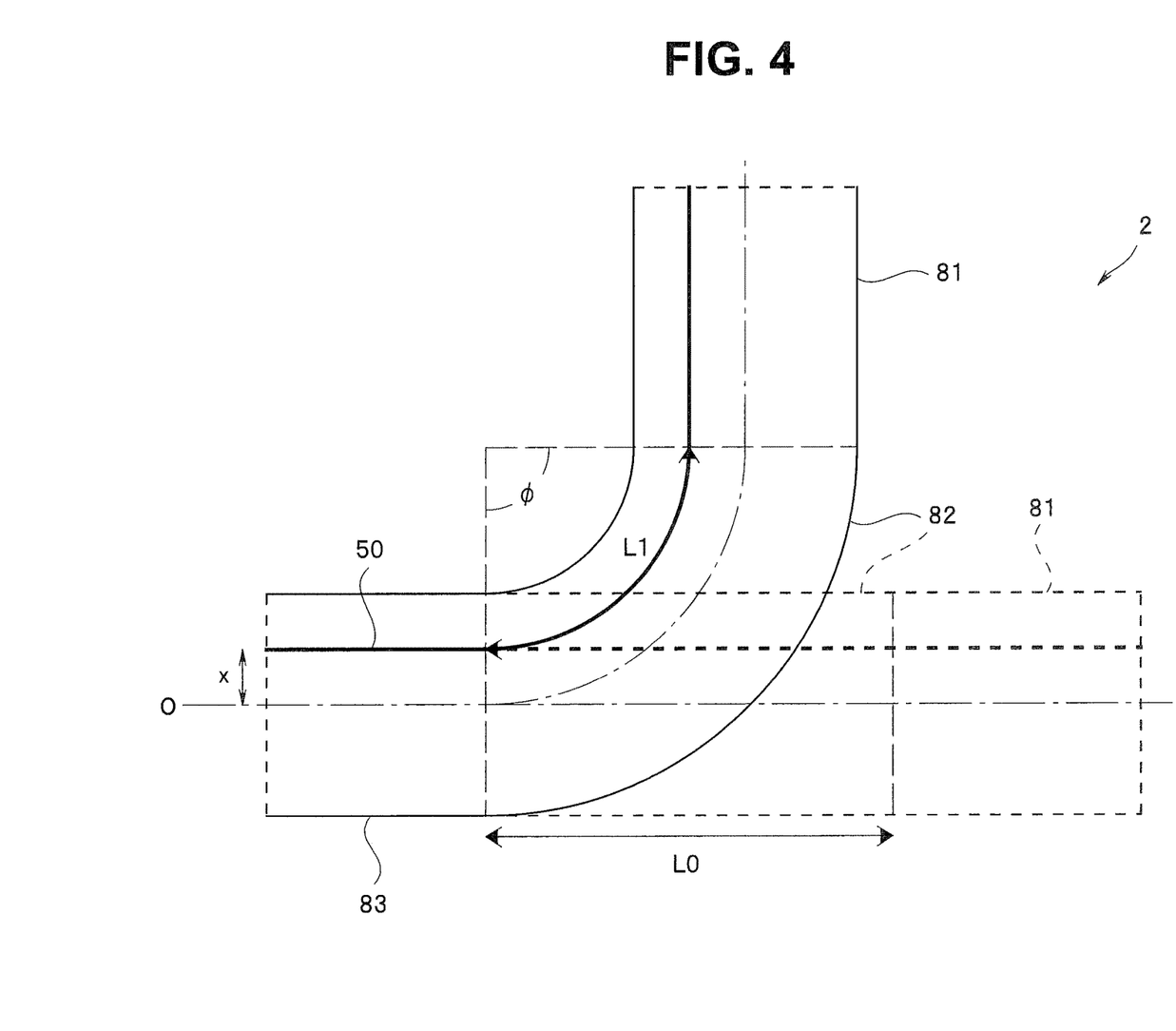
FIG. 4 is a cross-sectional view illustrating operations of the bending portion of the endoscope of the first embodiment.

A case will now be described in which, as shown in FIG. 4, the bending portion 82 bends in the (B) direction and a bending angle is an angle φ. As a premise, it is assumed that even if the scope bends, the length at the scope center (x=0) does not change and remains L0. When the insertion path of the optical fiber 50 is separated by a deviation amount x from a center line O of the bending portion 82, the path length L decreases from L0 to L1.

$$L1 = L0 - \Delta L \quad \text{(Equation 1)}$$

Where, $\Delta L = 2\pi x(\phi/360)$

That is, $\Delta L$ depends on the deviation amount x and the bending angle $\phi$. For example, if the deviation amount x=5 mm and the bending angle $\phi$=180 degrees, $\Delta L \approx 15$ mm. Note that, although differing according to the specifications, in some cases a maximum bending angle $\phi$ of the bending portion 82 is equal to or greater than 360 degrees.

Figure 5:
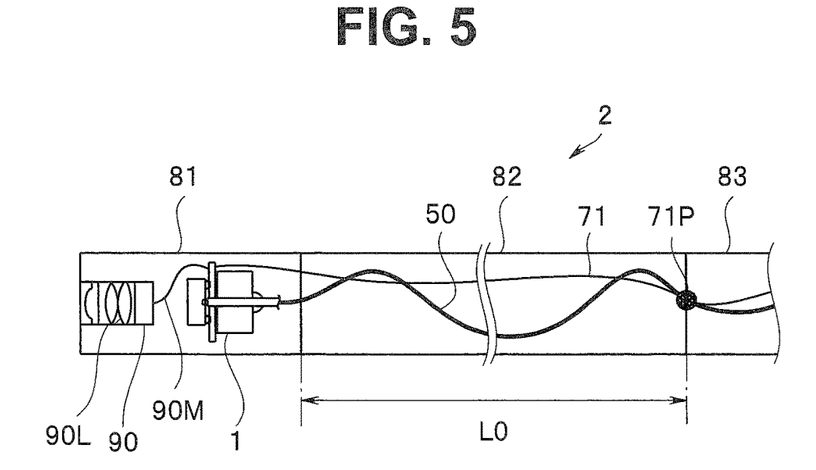
FIG. 5 is a cross-sectional view illustrating the configuration of the bending portion of the endoscope of the first embodiment.

As shown in FIG. 5, in the endoscope 2, a length in the bending portion 82 of the optical fiber 50 is designed so as to be longer than the length L0 of the bending portion, in other words, the length of a portion of the optical fiber 50 that is inserted through the inside of the bending portion 82 is designed so as to have so-called "play". That is, as shown in FIG. 5, with respect to the length L0 when the bending portion 82 is in a straight state, the optical fiber 50 is inserted through the inside of the bending portion 82 while meandering therethrough.

The length in the bending portion 82 of the optical fiber 50 is designed so as to be equal to or greater than L0+$\Delta$Lmax. The amount $\Delta$Lmax is the amount of deformation at the time of the maximum bending angle $\phi$max.

Note that, in consideration of an unexpected change in shape, it is more preferable that the length in the bending portion 82 of the optical fiber 50 is equal to or greater than L0+2×$\Delta$Lmax. However, to prevent entanglement with other members, it is preferable that the length is less than or equal to L0+5×$\Delta$Lmax.

Figure 6:
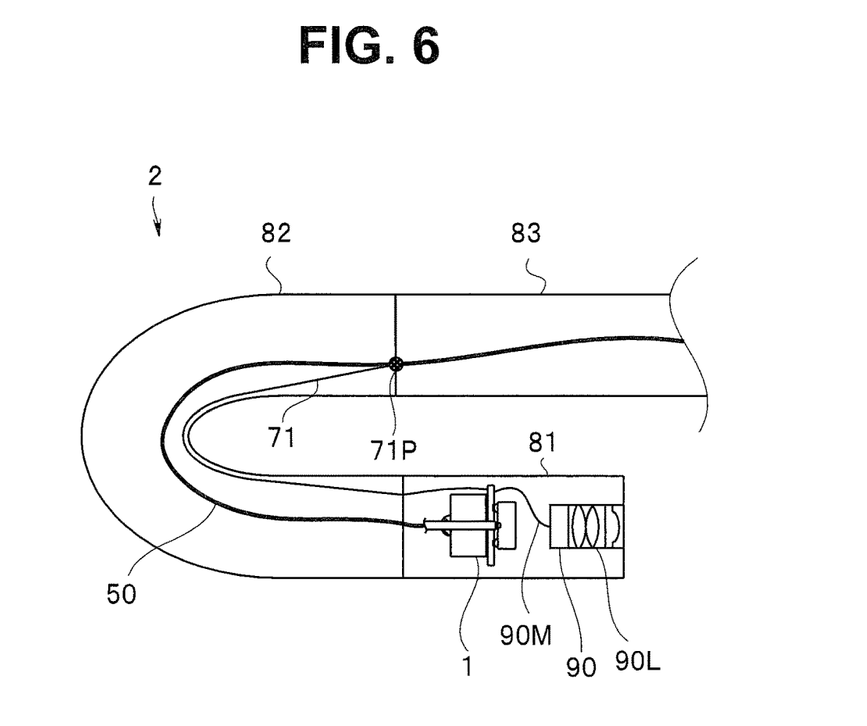
FIG. 6 is a cross-sectional view illustrating the configuration of the bending portion of the endoscope of the first embodiment.

As shown in FIG. 6, even if the bending portion 82 bends and changes shape, strong stress is not applied to the optical fiber 50. Therefore, the endoscope 2 can stably transmit optical signals.

Further, preferably the length of the optical fiber 50 at a portion that is inserted through the flexible portion 83 is also longer than the length of the flexible portion 83. For example, at the aforementioned portion, a length of the optical fiber 50 that is 110% or more and 150% or less relative to the length of the flexible portion 83 is particularly preferable. As long as the length of the optical fiber 50 at the aforementioned portion is equal to or greater than the aforementioned low limit, strong stress will not be applied to the optical fiber 50 by a change in the shape of the flexible portion 83, and as long as the length of the optical fiber 50 is less than or equal to the aforementioned upper limit, there is no risk of the optical fiber 50 entangling with another member inside the insertion portion 80, for example, an operation wire.

As shown in FIG. 5, the endoscope 2 further includes a wire element 71 having one end fixed to the optical transmission module 1 that is arranged in the rigid distal end portion 81. The wire element 71 is a wire whose length in the bending portion 82 is shorter than that of the optical fiber 50, and with respect to which elastic deformation is difficult. Since the optical fiber 50 is fixed by the wire element 71 and a fixing portion 71P on the proximal end portion side of the bending portion 82, the position thereof with respect to the insertion portion 80 is fixed.

The fixing portion 71P is constituted by adhesive, a binding band, a heat-shrinkable tube or a clip or the like. Further, as the fixing portion 71P, a configuration may also be adopted that makes it difficult for the optical fiber 50 to move, by winding the optical fiber 50 around an existing member. As long as the position of the fixing portion 71P is in the vicinity of the proximal end portion of the bending portion 82, the fixing portion 71P may be on the portion side of the flexible portion 83. Note that, in a case where the optical fiber 50 is disposed inside a protective tube (not illustrated), the fixing portion 71P may be provided on the outer surface of the protective tube, and not the optical fiber.

If the wire element 71 extends completely due to the bending portion 82 bending and changing shape, the endoscope 2 cannot be bent any further from that state. Consequently, even if the bending portion 82 changes shape in an unexpected manner, strong stress is not applied to the optical fiber 50. Further, in a case where the optical fiber 50 is disposed within the protective tube, since a situation does not arise in which strong stress is not applied to the protective tube, strong stress is not applied to the optical fiber 50 that is disposed therein.

Further, as shown in FIG. 3, when the bending portion 82 bends in the (C) direction, the path length L increases by an amount of $\Delta L$. Thereupon, the optical fiber 50 enters a state in which there is a large amount of slack in the optical fiber 50 in the bending portion 82. However, because the optical fiber 50 is fixed by the fixing portion 71P, the bending and change in shape of the bending portion 82 does not affect the portion of the optical fiber 50 that is inserted through the flexible portion 83. Further, the portion of the optical fiber 50 that is disposed in the bending portion 82 does not move into the flexible portion 83.

Therefore, there is no risk of the optical fiber 50 entangling with another member that is inserted through the insertion portion 80, for example, an operation wire.

Note that, an existing member that is inserted through the bending portion 82, for example, electric wiring, a channel, an air feeding tube or a water feeding tube may also be utilized as the wire element 71.

Figure 7:
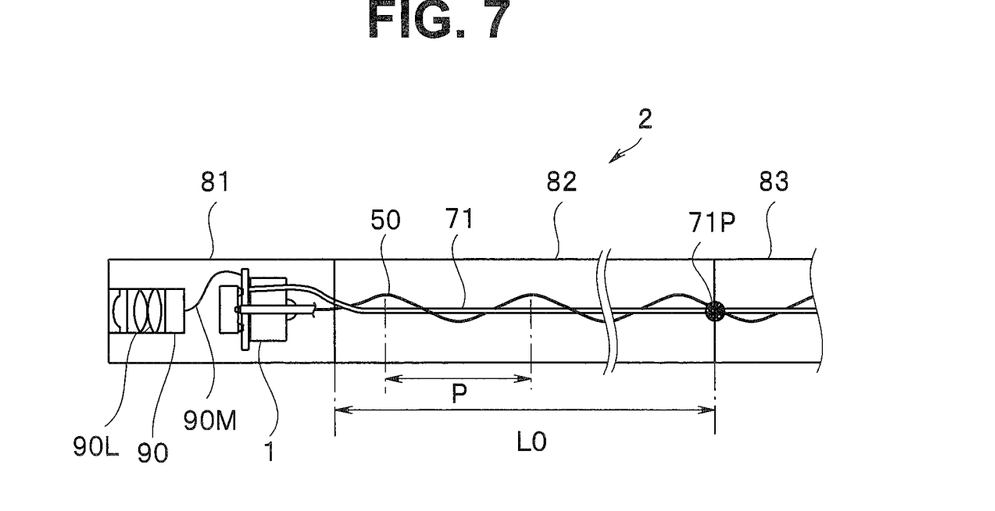
FIG. 7 is a cross-sectional view illustrating the configuration of the bending portion of the endoscope of the first embodiment.

The optical fiber 50 may meander in a wavelike shape, or may be wound around the wire element 71 and meander in a spiral shape. In the case of winding around the wire element 71, as shown in FIG. 7, it is desirable to provide a small amount of slack between the optical fiber 50 and the wire element 71, and it is desirable that a pitch (winding period) P of the winding is 10 mm or more. In this case, the wire element 71 may be thicker than or narrower than the optical fiber 50.

Further, in the flexible portion 83 also, the position of the optical fiber 50 with respect to the flexible portion 83 may be fixed at predetermined intervals.

<Modification of First Embodiment>

Figure 8:
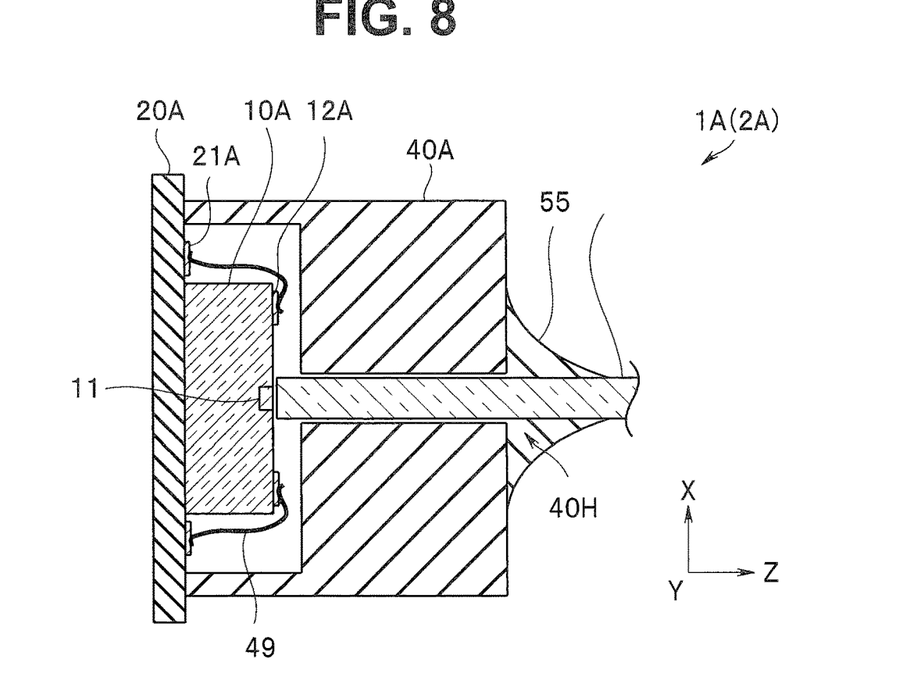
FIG. 8 is a cross-sectional view of an optical transmission module of an endoscope according to a modification of the first embodiment.

An endoscope 2A of the present modification has an optical transmission module 1A shown in FIG. 8.

In the optical transmission module 1A, an optical device 10A and a holding member 40A are arranged on one face of a wiring board 20A. An electrode 12A of the optical device 10A, and an electrode pad 21A of the wiring board 20A are connected with wire bonding wiring 49.

The holding member 40A that has a concave portion in which the optical device 10A is housed is joined through an adhesive layer (not illustrated) to the wiring board 20A so that the through hole 40H faces the light-emitting portion 11 of the optical device 10A.

Since it is not necessary to provide a hole that serves as an optical path in the wiring board, and it is only necessary to perform positioning between two components, namely, the optical device 10A and the holding member 40A, the optical transmission module 1A can be easily manufactured.

Further, the optical transmission module 1A can be miniaturized since the thickness of the optical transmission module 1A does not need to include a thickness amount corresponding to the thickness of the optical device 10A. In addition, although the configuration is one in which an adhesive area between the holding member 40A and the wiring board 20A is small and the adhesion strength is weak, because of stress relaxation with respect to the optical fiber 50, there is no risk of an adhesive point on the holding member 40A peeling off.

<Second Embodiment>

Since an endoscope 2B of the second embodiment is similar to the endoscopes 1 and 1A, constituent elements having the same functions are assigned the same reference numerals, and a description thereof is omitted.

Figure 9:
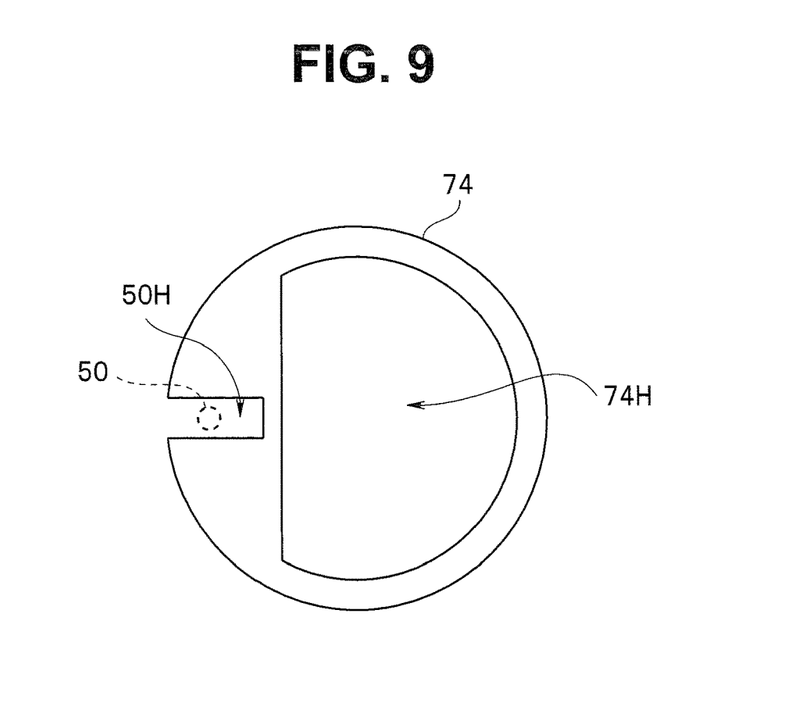
FIG. 9 is a top view of a guide member of an endoscope of a second embodiment.

In the endoscope 2B, a plurality of guide members 74 which define the position of the optical fiber 50 that is inserted through the insertion portion 80 are provided in the bending portion 82. As shown in FIG. 9, a substantially disk-shaped guide member 74 has a concave portion 50H through which the optical fiber 50 is inserted, and a hole portion 74H through which another member is inserted.

Figure 10:
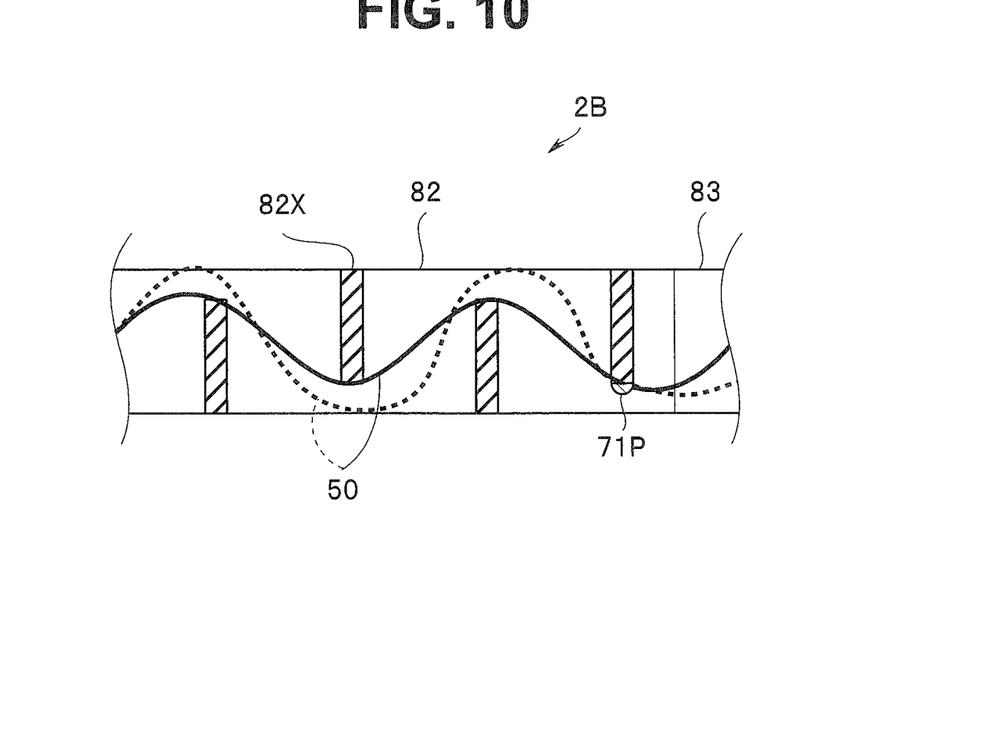
FIG. 10 is a cross-sectional view illustrating the configuration of a bending portion of the endoscope of the second embodiment.

Further, as shown in FIG. 10, the plurality of guide members 74 are arranged inside the insertion portion 80 (bending portion 82) at predetermined intervals so that the concave portions 50H are alternately positioned on the top and bottom (at opposing positions). Therefore, the optical fiber 50 that is inserted through the respective concave portions 50H is inserted through the insertion portion 80 while meandering by a large amount. The interval at which the guide members 74 are disposed is, for example, ½ to ⅕ the length of the bending portion 82.

Further, when tensile stress is applied, the optical fiber 50 releases the stress by changing the insertion path as indicated by a dashed line.

Figure 11:
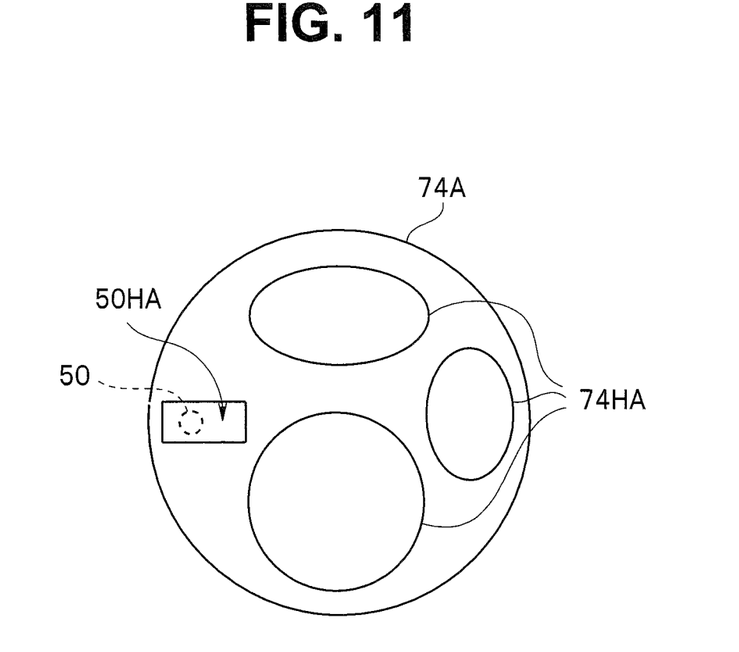
FIG. 11 is a top view of a different guide member of the endoscope of the second embodiment.

Note that, it is sufficient that the plurality of guide members 74 are disposed so that the optical fiber 50 that is inserted through the respective concave portions 50H thereof meanders. Further, with respect to the optical fiber 50 and another member which are both inserted through the insertion portion 80, the guide members preferably have a function that separates a position of the optical fiber 50 and a position of another member, since it is thereby difficult for the optical fiber 50 to become entangled with the other member. As long as the guide member has a function that defines a position of the optical fiber 50, for example, the guide member may be a guide member 74A illustrated in FIG. 11 that has a hole portion 50HA through which the optical fiber 50 is inserted, and a plurality of hole portions 74HA through which other members are inserted.

The guide members 74 may also be arranged in the flexible portion 83. The interval at which the guide members 74 are disposed in the flexible portion 83 may be longer than the interval at which the guide members 74 are disposed in the bending portion 82.

In addition, a single multi-lumen tube that is inserted though the bending portion 82 may be used as a guide member. That is, in the case of using a multi-lumen tube, a single guide member is sufficient.

<Third Embodiment>

Since an endoscope 2C of the third embodiment is similar to the endoscopes 1, 1A and 1B, constituent elements having the same functions are assigned the same reference numerals, and a description thereof is omitted.

Figure 12:
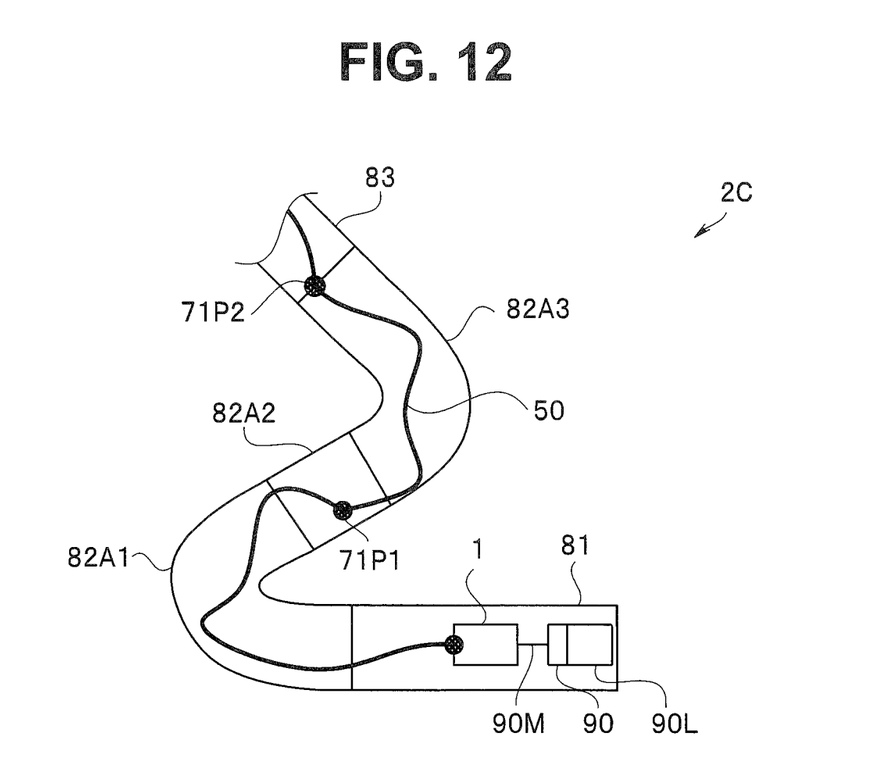
FIG. 12 is a cross-sectional view illustrating the configuration of a bending portion of an endoscope of a third embodiment.

As shown in FIG. 12, the endoscope 2C includes two bending portions 82A1 and 82A3 so as to enable observation of a specific direction in a narrow space into which the rigid distal end portion 81 is inserted. The bending portions 82A1 and 82A3 are connected, for example, through an intermediate portion 82A2.

Not only is the position of the optical fiber 50 with respect to the insertion portion 80 fixed by a fixing portion 71P2 in the proximal end portion of the bending portion 82A3, but the position of the optical fiber 50 with respect to the insertion portion 80 is also fixed in the intermediate portion 82A2 between the two bending portions by a fixing portion 71P1.

The endoscope 2C has the two bending portions 82A1 and 82A3, and although each of the two bending portions 82A1 and 82A3 bends and changes shape, similarly to the endoscope 1, there is no risk of the optical fiber 50 that is inserted through the inside thereof receiving a large amount of stress or becoming entangled with another member. Therefore, the endoscope 2C can stably transmit optical signals.

Note that, even in the case of an endoscope having three or more bending portions, naturally the endoscope will have the same advantageous effects as the endoscope 2C as long as the position of the optical fiber 50 with respect to the insertion portion 80 is fixed between the plurality of bending portions.

The present invention is not limited to the above described embodiments and modifications and the like, and various changes, combinations and applications are possible within a range that does not deviate from the gist of the present invention.

What is claimed is:

1. An endoscope comprising:
   an insertion portion in which a rigid distal end portion, a bending portion for changing a direction of the rigid distal end portion, and a flexible portion are provided in a connected row arrangement from a distal end to a proximal end of the insertion portion;
   an optical fiber that is inserted through the insertion portion and is configured to transmit an optical signal;
   an image sensor disposed in the distal rigid end portion;
   an optical transmission module disposed in the rigid distal end portion to receive an electrical signal from the image sensor, the optical transmission module having an optical device in which a light-emitting portion configured to convert the electrical signal into the optical signal is formed, and a holding member having a through hole, the holding member being disposed so that the through hole is positioned over the light-emitting portion a distal end portion of the optical fiber being inserted into and fixed in the through hole of the holding member; and
   electric wiring disposed in the insertion portion, the electric wiring comprising a wire having both a protecting function for protecting the optical fiber and for providing an electric wiring function, the wire having one end fixed in the rigid distal end portion, the wire having a length inside the bending portion that is shorter than a length of the optical fiber inside the bending portion;
   wherein the length of the optical fiber in the bending portion is longer than a length of the bending portion;
   a position of the optical fiber is fixed, with respect to the insertion portion, on a proximal end portion of the bending portion between the rigid distal end portion and the flexible portion of the insertion portion; and
   the optical fiber is fixed to the wire on the proximal end portion of the bending portion such that the wire protecting the optical fiber by reducing a stress in the optical fiber when the bending portion is bent.

2. The endoscope according to claim 1, further comprising:
a guide member configured to define a position of the optical fiber inside the bending portion,
wherein the optical fiber that is inserted through inside of the bending portion while meandering through the inside of the bending portion is fixed to the guide member on the proximal end portion.

3. The endoscope according to claim 1, further comprising:
a wiring board having a first principal surface and a second principal surface, in which the optical device and the first principal surface are fixed, and the holding member and the second principal surface are fixed, and having a hole at a position facing the through hole and the light-emitting portion.

4. The endoscope according to claim 1, wherein:
the insertion portion comprises first and second bending portions, each provided distally relative to the rigid distal end portion and the flexible portion, and
the optical fiber is fixed with respect to the insertion portion at a position between the first and second bending portions.

5. An insertion portion for use with an endoscope, the insertion portion comprising:
a rigid distal end portion, a bending portion for changing a direction of the rigid distal end portion, and a flexible portion are provided in a connected row arrangement from a distal end to a proximal end of the insertion portion;
an optical fiber that is inserted through the flexible portion, bending portion and rigid distal end portion, and is configured to transmit an optical signal;
an image sensor disposed in the distal rigid end portion;
an optical transmission module disposed in the rigid distal end portion to receive an electrical signal from the image sensor, the optical transmission module having an optical device in which a light-emitting portion configured to convert the electrical signal into the optical signal is formed, and a holding member having a through hole, the holding member being disposed so that the through hole is positioned over the light-emitting portion a distal end portion of the optical fiber being inserted into and fixed in the through hole of the holding member; and
electric wiring disposed in the insertion portion, the electric wiring comprising a wire having both a protecting function for protecting the optical fiber and for providing an electric wiring function, the wire having one end fixed in the rigid distal end portion, the wire having a length inside the bending portion that is shorter than a length of the optical fiber inside the bending portion;
wherein the length of the optical fiber in the bending portion is longer than a length of the bending portion;
a position of the optical fiber is fixed on a proximal end portion of the bending portion between the rigid distal end portion and the flexible portion; and
the optical fiber is fixed to the wire on the proximal end portion of the bending portion such that the wire protecting the optical fiber by reducing a stress in the optical fiber when the bending portion is bent.

6. The endoscope according to claim 1, wherein the length in the bending portion of the optical fiber is equal to or greater than L0+2times ΔLmax and less than or equal to L0+5times ΔLmax, the amount ΔLmax is the amount of deformation at the time of the maximum bending angle Φmax.

* * * * *